United States Patent

Rendenbach-Mueller et al.

[11] Patent Number: 5,071,864
[45] Date of Patent: Dec. 10, 1991

[54] AMINOALKYL-SUBSTITUTED 2-AMINOTHIAZOLES AND THERAPEUTIC AGENTS CONTAINING THEM

[75] Inventors: Beatrice Rendenbach-Mueller, Waldsee; Liliane Unger, Ludwigshafen; Hans-Juergen Teschendorf, Dudenhofen, all of Fed. Rep. of Germany

[73] Assignee: BASF Aktiengesellschaft, Ludwigshafen, Fed. Rep. of Germany

[21] Appl. No.: 544,900

[22] Filed: Jun. 28, 1990

[30] Foreign Application Priority Data

Jul. 18, 1989 [DE] Fed. Rep. of Germany ....... 3923675

[51] Int. Cl.$^5$ ............... A61K 31/425; C07D 277/18
[52] U.S. Cl. ................................ 514/370; 514/252; 514/326; 514/342; 544/295; 544/360; 544/369; 546/209; 546/280; 548/190; 548/193; 548/198
[58] Field of Search ............ 544/369, 295, 360; 546/209, 280; 514/252, 326, 342, 370; 548/190, 198, 193

[56] References Cited

U.S. PATENT DOCUMENTS 4,935,424 6/1990 Caprathe et al. .................. 514/252

FOREIGN PATENT DOCUMENTS 0345533 12/1989 European Pat. Off. .

OTHER PUBLICATIONS

Szczycinski et al., Chem. Abst. 95-97851a (1981).
Ferrand et al., Chem. Abst. 85-46483t (1976).
Katritzky, Handbook of Heterocyclic Chemistry p. 424.
March, Advanced Organic Chem. 3rd Edition pp. 364-365; 370-371.

Primary Examiner—Cecilia Shen
Attorney, Agent, or Firm—Oblon, Spivak, McClelland, Maier & Neustadt

[57] ABSTRACT

Aminoaklyl-substituted 2-aminothiazole derivatives of the general formula I

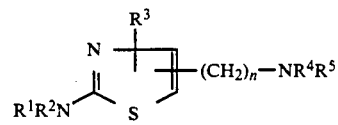

where
$R^1$ and $R^2$, which may be identical or different, are each hydrogen, $C_1$–$C_5$-alkyl, phenyl or $C_1$–$C_5$-alkanoyl, $R^3$ is $C_1$–$C_5$-alkyl, phenyl which is unsubstituted or monosubstituted by halogen, $C_1$–$C_5$-alkyl or $C_1$–$C_5$-alkoxy, or thienyl,
n is an integer of from 2 to 6, and
$NR^4R^5$ is one of the groups a, b, c or d

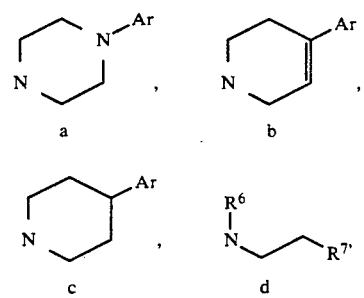

where Ar is a phenyl ring which is unsubstituted or monsubstituted by $C_1$–$C_5$-alkyl, $C_1$–$C_5$-alkoxy, halogen, hydroxyl, nitro or trifluoromethyl, or is pyridyl, pyrimidinyl or thienyl, $R^5$ is H or $C_1$–$C_5$-alkyl and $R^7$ is phenyl which is unsubstituted or monosubstituted by $C_1$–$C_5$-alkyl, $C_1$–$C_5$-alkoxy, halogen, hydroxyl or trifluoromethyl, or $R^7$ is thienyl, with the proviso that $R^3$ is $C_1$–$C_5$alkyl only when either $R^1$ and $R^2$ are not both simultaneously H or when $NR^4R^5$ is the group d, and their salts with physiologically tolerated acids, their preparation, their use for the preparation of a drug, and the drugs.

5 Claims, No Drawings

AMINOALKYL-SUBSTITUTED 2-AMINOTHIAZOLES AND THERAPEUTIC AGENTS CONTAINING THEM

The present invention relates to aminoalkylsubstituted 2-aminothiazoles of the general formula I, which have valuable therapeutic properties and are particularly suitable for the treatment of disorders associated with high blood pressure and of disorders of the central nervous system, and therapeutic agents based on these compounds.

PL 106 675 describes piperazinylethyl-2-aminothiazoles as neuroleptic agents. They have a dopamineantagonistic action.

EP 345 533 describes similarly substituted 2-aminothiazoles, inter alia as dopamine agonists. However, their actions are not satisfactory in all cases.

It is an object of the present invention to provide novel active compounds having better pharmacological properties.

We have found that this object is achieved by the aminoalkyl-substituted 2-aminothiazoles of the formula I as claimed in claim 1.

In the general formula I

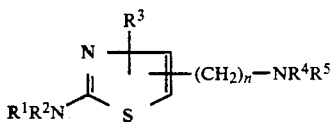

$R^1$ and $R^2$, which may be identical or different, are each hydrogen, $C_1$-$C_5$-alkyl, phenyl or $C_1$-$C_5$-alkanoyl, $R^3$ is $C_1$-$C_5$-alkyl, phenyl which is unsubstituted or monosubstituted by halogen, $C_1$-$C_5$-alkyl or $C_1$-$C_5$-alkoxy, or thienyl,
n is an integer of from 2 to 6, and
$NR^4R^5$ is one of the groups a, b, c or d

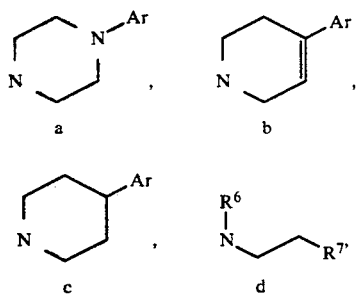

where Ar is a phenyl ring which is unsubstituted or monosubstituted by $C_1$-$C_5$-alkyl, $C_1$-$C_5$-alkoxy, halogen, nitro, hydroxyl or trifluoromethyl or is pyridyl, pyrimidinyl or thienyl, $R^6$ is H or $C_1$-$C_5$-alkyl and R is phenyl which is unsubstituted or monosubstituted by $C_1$-$C_5$-alkyl, $C_1$-$C_5$-alkoxy, halogen, hydroxyl or trifluoromethyl or $R^7$ is thienyl, and their salts with physiologically tolerated acids. The proviso here is that $R^3$ is $C_1$-$C_5$-alkyl only when either $R^1$ and $R^2$ are not both simultaneously H or when $NR^4R^5$ is the group d.

Halogen is fluorine, chlorine, bromine and (less preferably) iodine.

The compounds of the general formula I can be prepared, for example, if a) an α-haloketone of the general formula II

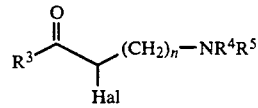

where $R^3$, $R^4$, $R^5$ and n are as defined at the outset and Hal is chlorine, bromine or iodine, or a salt of this compound with a hydrohalic acid is reacted with a thiourea of the general formula III

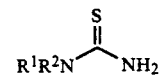

where $R^1$ and $R^2$ are as defined at the outset, or b) a compound of the general formula IV

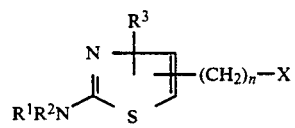

where $R^1$, $R^2$, $R^3$ and n are as defined at the outset and X is a nucleofugic leaving group, such as chlorine, bromine or $R^8SO_2O$ and $R^8$ here is lower alkyl or is phenyl which is unsubstituted or substituted by $C_1$-$C_3$-alkyl or halogen, is reacted with an amine of the general formula V $$HNR^4R^5 \qquad V$$

where $R^4$ and $R^5$ have the stated meanings, or c) a 2-aminothiazole of the general formula VI

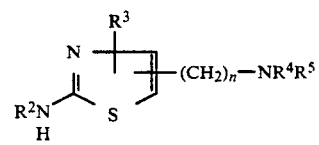

where $R^2$, $R^3$, $R^4$, $R^5$ and n are as defined at the outset, is alkylated with an alkylating reagent $R^1$-X or $R^1_2SO_4$ or with an aldehyde RCHO in the presence of a reducing agent or is acylated with an acylating agent

In the case of process a), the reactions are preferably carried out in a solvent at from room temperature to the boiling point of the solvent used, in the presence or absence of an acid acceptor. Examples of suitable solvents are aliphatic alcohols, dimethylformamide, glacial acetic acid, water or a solvent mixture, and suitable acid acceptors are inorganic bases, such as sodium carbonate, potassium carbonate or tertiary organic bases, such as triethylamine or pyridine. The latter may simultaneously serve as a solvent when used in excess. The reaction product can be obtained in a conventional manner, for example by filtration, distilling off the solvent or extraction from the reaction mixture. The compound obtained is purified in a conventional manner, for example by recrystallization from a solvent, chromatography or conversion into an acid addition compound.

The α-haloketones of the general formula II which are used as starting materials are obtained by halogenation of the corresponding ketones of the general formula VII

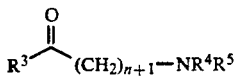
VII where $R^3$, $R^4$, $R^5$ and n have the stated meanings. Halogenation is preferably carried out using an equimolar amount of chlorine, bromine or iodine. The resulting compounds of the formula II need not be further purified.

In the case of process b), the reactions are carried out in the melt, if desired also in the presence of a solvent, eg. ethyl acetate, tetrahydrofuran, dimethylformamide, dimethoxyethane, toluene or xylene, at from room temperature to the boiling point of the solvent used, preferably in the presence of a base, such as sodium methylate, sodium ethylate, sodium hydride, sodium carbonate or potassium carbonate, or of an amine, eg. pyridine. The amine component V in excess may also act as reagent, base and solvent. Some of the compounds of the formula IV which are used as starting materials are described in the literature or can be prepared in a similar manner, for example by halogenation of an ω-chloroketone of the general formula VIII

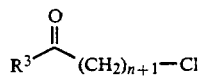
VIII where $R^3$ and n have the stated meanings, and subsequent reaction of the haloketone with a thiourea derivative of the formula III.

The reactions of process c) are carried out by methods known for the alkylation and acylation of amines from the literature. The components may be melted together in the absence of a solvent. However, it is also possible to carry out the reaction in the presence of an inert solvent, for example of an aromatic hydrocarbon, such as toluene or xylene, of an ether, such as tetrahydrofuran or dioxane, of a ketone, such as acetone or butanone, of an amide, such as dimethylformamide or N-methylpyrrolidone, or of a nitrile, such as acetonitrile. The addition of an acid acceptor, for example of a hydroxide, carbonate or amine, such as triethylamine or pyridine, is advantageous. In a variant of the above method, an aldehyde can be used as the alkylating agent, with the addition of a suitable reducing agent, preferably sodium boranate or sodium cyanoborohydride, under the reaction conditions known from the literature for reductive amination. Compounds of the formula VI can be converted into the corresponding N-acyl derivatives by means of an acylating agent. Particularly suitable acylating agents are appropriate halides (for example acyl chlorides and bromides) and anhydrides. Acylation is preferably carried out in solution or suspension using inert solvents, for example ethers, such as diethyl ether, tetrahydrofuran or dioxane, halohydrocarbons, such as 1,2-dichloroethane or chlorobenzene, hydrocarbons, such as toluene, or dimethylformamide, acetonitrile or solvent mixtures, advantageously in the presence of a base, for example of an alkali metal hydroxide or alkaline earth metal hydroxide, of an alkali metal carbonate or of an amine. The acylation can also be carried out using esters, preferably methyl esters of the corresponding acids, advantageously in one of the abovementioned solvents or excess ester.

If necessary, the novel compounds obtained are converted into their acid addition salts with physiologically tolerated acids. Suitable conventional physiologically tolerated organic and inorganic acids are, for example, hydrochloric acid, hydrobromic acid, phosphoric acid, sulfuric acid, oxalic acid, maleic acid, fumaric acid, lactic acid, tartaric acid, adipic acid and benzoic acid. Further acids are described in Fortschritte der Arzneimittelforschung, Vol. 10, page 224 et seq., Birkhäuser Verlag, Basel and Stuttgart, 1966.

The acid addition salts are as a rule obtained in a conventional manner by mixing the free base or a solution thereof with the corresponding acid or a solution thereof in an organic solvent, for example a lower alcohol, such as methanol, ethanol or propanol, an ether, such as ethyl tert-butyl ether, a ketone, such as acetone or methyl ethyl ketone, or an ester, such as ethyl acetate. For better crystallization, mixtures of the stated solvents may also be used. Moreover, pharmaceutically acceptable aqueous solutions of acid addition compounds of the novel compounds I can be prepared by dissolving the free bases in an aqueous acid solution.

Receptor binding test

Striata from rats (Sprague Dawley, Charles River) were homogenized in 0.32 M sucrose solution (0° C.) immediately after removal. The homogenate was filtered over gauze, the filtrate was centrifuged at 1,000 g (5 min at 4° C.) and the resulting supernatant was centrifuged at 40,000 g (10 min, 4° C.). The residue (membranes) was taken up in incubation buffer (50 mM trisHCl, 1 mM $MgCl_2$ and 0.1% ascorbic acid, pH 7.4) and incubated for 20 min at 37° C. Washing was then carried out twice with incubation buffer by resuspension and recentrifuging. The membranes were frozen in portions in liquid nitrogen.

The test batches (1 ml) were composed of membranes (380 μg of protein), 1 nM $^3$H-ADTN (NEN, Dreieich Germany, specific radioactivity 1.4 TBq/mmol) and 0.1 μM SCH 23390 (total binding) or a) additionally with 50 nM spiperone (nonspecific binding) or b) with test substance. The batches were prepared in triplicate.

After the end of incubation (40 min at 25° C.), the batches were filtered over glass fiber filters (Whatman GF/B) and washed briefly with ice cold wash buffer (trisHCl, pH 7.4). The radioactivity retained on the filters was determined by liquid scintillation measurement. The nonspecific binding was about 40-50% of the total binding.

Evaluation of the competition curves and determination of the dissociation constant were carried out by iterative nonlinear regression analysis similarly to the program Ligand (Muson and Rodbard: Anal. Biochem. 107 (1980), 220).

| Example | Ki (nM) |
| --- | --- |
| 1 | 6 |
| 2 | 20 |
| 3 | 4 |
| 4 | 16 |
| 5 | 10 |
| 8 | 10 |
| 9 | 14 |
| 10 | 10 |
| 11 | 10 |
| 13 | 10 |

-continued

| Example | Ki (nM) |
| --- | --- |
| 14 | 15 |
| 18 | 25 |
| 22 | 16 |
| 23 | 20 |
| 25 | 4 |

The novel compounds are suitable for the treatment of disorders, in particular for the treatment of disorders associated with high blood pressure and disorders of the central nervous system (for example Parkinson's disease and schizophrenia). They have, in particular, useful dopaminergic activity. The tests used show that the substances of the general formula I have dopamine-agonistic activity with selectivity for presynaptic dopamine receptors. The compounds of the formula I show high affinity to the $D_2$-receptor; they inhibit the motility in mice (measured in light barrier cages) and influence the rotation behavior in rats with one-sided 6-hydroxydopamine lesions of the Substantia nigra (Ungerstedt, U. and Abuthnott, G.W., Brain Research 24 (1970), 485–493).

The novel compounds can be administered orally or parenterally (subcutaneously, intravenously, intramuscularly or intraperitoneally) in a conventional manner. Administration may also be effected through the nasopharangyl space using vapors or sprays.

The dose depends on the age, condition and weight of the patient and on the route of administration. As a rule, the daily dose of active compound is about 10–500 mg per patient per day in the case of oral administration and about 1–500 mg per patient per day in the case of parenteral administration.

The novel compounds may be employed in the conventional solid or liquid pharmaceutical forms, such as tablets, film tablets, capsules, powders, granules, coated tablets, suppositories, solutions or sprays. These are prepared in a conventional manner, and to do so the active compounds can be mixed with the conventional pharmaceutical auxiliaries, such as tablet binders, fillers, preservatives, tablet disintegrants, flow regulators, plasticizers, wetting agents, dispersants, emulsifiers, solvents, retarding agents, antioxidants and/or propellants (cf. H. Sucker et al.: Pharmazeutische Technologie, Thieme-Verlag, Stuttgart, 1978). The formulations thus obtained normally contain from 1 to 99% by weight of the active compound.

EXAMPLES

EXAMPLE 1

2-Methylamino-4-methyl-5-[3-(4-phenylpiperazin-1-yl)-propyl]-thiazole dihydrochloride 20 mmol of 6-(4-phenylpiperazin-1-yl)-hexan-2-one in 65 ml of glacial acetic acid were initially taken, and 11.6 ml of HBr/glacial acetic acid (33%) were added while cooling with ice. 3.3 g of bromine in 36 ml of glacial acetic acid were then added dropwise at room temperature. The reaction mixture was stirred for 1 hour at room temperature and evaporated down, the crude 3-bromo-6-(4-phenylpiperazin-1-yl)-hexan-2-one was taken up in ethanol, 22.3 mol of thiourea were added and refluxing was carried out for 5 hours. The solid which crystallized out after cooling was partitioned in 2 N NaOH/$CH_2Cl_2$. The organic phase was separated off, washed with $H_2O$, dried over $CaCl_2$ and evaporated down. The residue was taken up in ethanol and 3 N HCl in ether was added. The product which crystallized out was filtered off under suction and dried.

Yield 36%; mp. 302° C. (decomposition)

Elemental analysis: $C_{18}H_{23}N_3S \cdot 2HCl \cdot H_2O$ Calculated C 51.30 H 7.18 Cl 16.82 N 13.29 O 3.80 S 7.61 Found C 51.0 H 7.2 Cl 16.9 N 13.0 O 3.9 S 7.4

EXAMPLE 2

2-Amino-4-methyl-5-[3-(N-methyl-N-phenethylamino)-propyl]-thiazole fumarate 25 mmol of 2-amino-5-(3-chloropropyl)-4-methylthiazole hydrochloride, 25 mmol of N-methylphenethylamine, 7 ml of triethylamine, 2.6 g of $Na_2CO_3$ and a pinch of NaI in 70 ml of ethanol were refluxed for 72 hours. The insoluble salts were filtered off, the filtrate was evaporated down and the residue was dissolved in isopropanol. 5.2 g of fumaric acid, dissolved in isopropanol, were added, and the solid which separated out thereafter was filtered off under suction and dissolved in ethanol while hot, and the insoluble constituents were separated off. The solid which crystallized out after the solution had been cooled was filtered off under suction and dried.

Yield: 38%; mp. 95°–98° C. (decomposition)

The Examples below were prepared similarly. The products were isolated in the form of the free base or of a salt with the conventional acids.

EXAMPLE 3

4-methyl-2-phenylamino-5-[3-(4-phenyl-1,2,3,6-tetrahydropyridyl)-propyl]-thiazole dihydrochloride Yield: 22%; mp. 236° C. (decomposition; acetone, methyl tert-butyl ether)

EXAMPLE 4

2-Amino-4-(4-methoxyphenyl)-5-[2-(4-phenyl-1,2,3,6-tetrahydropyridyl)-ethyl]-thiazole Yield: 19%; mp. 163° C. (decomposition; methanol)

EXAMPLE 5

2-Amino-5-[2-(4-phenyl-1,2,3,6-tetrahydropyridyl)-ethyl]-4-thien-2-ylthiazole dihydrochloride Yield: 33%; mp. 280° C. (ethanol)

EXAMPLE 6

2-Amino-4-(4-chlorophenyl)-5-[2-(4-phenyl-1,2,3,6-tetrahydropyridyl)-ethyl]-thiazol dihydrochloride Yield: 28%; mp. 172° C. (decomposition; ethanol)

EXAMPLE 7

2-Amino-4-phenyl-5-[4-(4-phenyl-1,2,3,6-tetrahydropyridyl)-butyl]-thiazole dihydrochloride Yield: 28%; mp. 140° C. (decomposition; isopropanol, methyl tert-butyl ether)

EXAMPLE 8

2-Amino-4-phenyl-5-[2-(4-phenyl-1,2,3,6-tetrahydropyridyl)-ethyl]-thiazole tartrate 20 mmol of 2-amino-5-(2-chloroethyl)-4-phenylthiazole and 20 mmol of 4-phenyl-1,2,3,6-tetrahydropyridine were thoroughly mixed and were heated under an $N_2$ atmosphere at 120° C. until conversion was complete, which was the case after 20 minutes. After cooling, the solidified melt was stirred with water, the oily solid residue was separated off and stirred thoroughly with methanol and the solid was filtered off under suction. The filter residue was partitioned in 2 N NaOH/CH$_2$Cl$_2$ and the organic phase was separated off, dried and evaporated down. The residue was dissolved in methanol while hot, one equivalent of tartaric acid was added and the precipitated solid was filtered off under suction and purified by recrystallization from ethyl acetate.

Yield: 20%; mp. 132°–133° C.

The Examples below were prepared similarly. If necessary, working up and purification of the crude product were varied. Among the methods used were conventional methods such as column chromatography or extraction at various pHs. The products were isolated in the form of the hydrochlorides, fumarates or tartrates.

EXAMPLE 9

2-Amino-4-phenyl-5-[3-(4-phenylpiperazin-1-yl)-propyl]-thiazole trihydrochloride Yield 22%; mp. 185° C. (ethanol)

EXAMPLE 10

2-Amino-4-methyl-5-[3-(N-phenethyl-N-propylamino)-propyl]-thiazole fumarate 1.5 equivalents of N-propylphenethylamine were used.

Yield: 21%; mp. 95°–98° C. (decomposition; methyl tert-butyl ether)

EXAMPLE 11

2-Amino-4-methyl-5-[3-(4-phenyl-1,2,3,6-tetrahydropyridyl)-propyl]-thiazole tartrate Yield: 27%; mp. 135°–136° C. (methanol)

EXAMPLE 12

2-Amino-4-phenyl-5-[2-(4-pyrimid-2-ylpiperazin-1-yl)-ethyl]tartrate

Yield: 26%; mp. 123°–124° C. (methanol)

EXAMPLE 13

2-Amino-4-phenyl-5-[3-(4-pyrimid-2-ylpiperazin-1-yl)-propyl]-thiazole tartrate

Yield: 24%; mp. 127°–128° C. (ethyl acetate)

EXAMPLE 14

2-Amino-4-phenyl-5-[3-(4-pyrid-2-ylpiperazin-1-yl)-propyl]tartrate

Yield: 22%; mp. 125°–126° C. (ethyl acetate)

EXAMPLE 15

2-Amino-4-phenyl-5-[2-(4-phenylpiperidin-1-yl)-ethyl]-thiazole tartrate

Yield: 24%; mp. 119°–120° C. (ethyl acetate)

EXAMPLE 16

2-Amino-5-[2-(4-(4-fluorophenyl)-piperazin-1-yl)-ethyl]-4-phenylthiazole tartrate Yield: 25%; mp. 130°–131° C. (ethyl acetate)

EXAMPLE 17

2-Amino-5-[3-(4-(4-fluorophenyl))-piperazin-1-yl)-propyl]-4-phenylthiazole tartrate Yield: 27%; mp. 129°–130° C. (methanol)

EXAMPLE 18

2-Amino-5-[3-(4-(2-chlorophenyl)-piperazin-1-yl)-propyl]-4-phenylthiazole tartrate Yield: 20%; mp. 122°–123° C. (methanol)

EXAMPLE 19

2-Amino-5-[2-(4-(4-methylphenyl)-piperazin-1-yl)-ethyl]-4-phenylthiazole tartrate Yield: 21%; mp. 122°–123° C. (ethyl acetate)

EXAMPLE 20

2-Amino-5-[2-(4-(4-methoxyphenyl)-piperazin-1-yl)-ethyl]-4-phenylthiazole tartrate Yield: 24%; mp. 124°–125° C. (methanol)

EXAMPLE 21

2-Amino-5 TM [3-(4-(3-methoxyphenyl)-piperazin-1-yl)-propyl]-4-phenylthiazole tartrate Yield: 27%; mp. 142°–144° C. (ethyl acetate)

EXAMPLE 22

2-Amino-5-[2-(4-(2-nitrophenyl)-piperazin-1-yl)-ethyl]-4-phenylthiazole tartrate Yield: 24%; mp. 121°–122° C. (ethyl acetate)

EXAMPLE 23

2-Amino-4-phenyl-5-[3-(N-propyl-N-phenethylamino)-propyl]-thiazole dihydrochloride 3 equivalents of N-propylmethylamine were used.
Yield: 41%; mp. 95° C. (decomposition; ethyl acetate)

EXAMPLE 24

2-Acetylamino-4-phenyl-5-[3-(N-propyl-N-phenethylamino)-propyl]-thiazole tartrate 2 equivalents of N-propylphenethylamine were used.
Yield: 46%; mp. 65° C. (decomposition; methyl tert-butyl ether)

EXAMPLE 25

2-Amino-4-methyl-5-[4-(N-propyl-N-phenethylamino)-butyl]-thiazole dihydrochloride 3 equivalents of N-propylphenethylamine were used.
Yield: 33%; mp. 125° C. (decomposition; acetone)

EXAMPLE 26

2-Amino-4-phenyl-5-[4-(N-propyl-N-phenethylamino)-butyl]-thiazole dihydrochloride 2.5 equivalents of N-propylphenethylamine were used.
Yield: 29%; mp. 80°–83° C. (ethyl acetate)

EXAMPLE 27

2-Amino-4-methyl-5-[5-(N-propyl-N-phenethylamino)-pentyl]-thiazole fumarate 3.5 equivalents of N-propylphenethylamine were used.
Yield: 31%; mp. 174°–175° C. (ethanol)

EXAMPLE 28

2-Amino-4-phenyl-5-[2-(4-pyrid-2-yl)-piperazin-1-yl)-ethyl]-thiazole tartrate

Yield: 21%; mp. 108°–110° C. (methanol)

EXAMPLE 29

2-Amino-5-[2-(4-(3-chlorophenyl)-piperazin-1-yl)-ethyl]-4-phenylthiazole tartrate Yield: 21%; mp. 122°-123° C. (ethyl acetate)

Examples of pharmaceutical forms:

A) Tablets having the following composition are pressed on a tabletting press in a conventional manner:

40 mg of the substance of Example 1

120 mg of corn starch 13.5 mg of gelatine 45 mg of lactose 2.25 mg of Aerosil ® (chemically pure silica in the form of submicroscopic particles)

6.75 mg of potato starch (as 6% strength paste)

B) 20 mg of the substance of Example 5

60 mg of core material 60 mg of sugar-coating material

The core material consists of 9 parts of corn starch, 3 parts of lactose and 1 part of a 60 : 40 vinylpyrrolidone/vinyl acetate copolymer. The sugar-coating material consists of 5 parts of sucrose, 2 parts of corn starch, 2 parts of calcium carbonate and 1 part of talc. The coated tablets thus produced are then provided with a coating resistant to gastric fluid.

C) 10 g of the substance of Example 7 are dissolved in 5,000 ml of water with the addition of NaCl and the solution is brought to pH 6.0 with 0.1 N NaOH, so that a blood-isotonic solution is formed. 1 ml portions of this solution are filled into ampoules and sterilized.

We claim:

1. An aminoalkyl-substituted 2-aminothiazole compound of the formula:

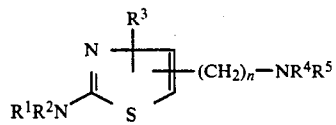

wherein $R^1$ and $R^2$, which may be identical or different, are each hydrogen, $C_1-C_5$-alkyl, phenyl or $C_1-C_5$-alkanoyl, $R^3$ is $C_1-C_5$-alkyl, phenyl which is unsubstituted or monosubstituted by fluorine, chlorine, bromine, $C_1-C_5$-alkyl, $C_1-C_5$-alkoxy or thienyl, n is an integer of from 2 to 6 and $NR^4R^5$ is of the formula:

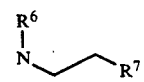

wherein $R^6$ is hydrogen or $C_1-C_5$-alkyl and $R^7$ is phenyl, which is unsubstituted or monosubstituted by $C_1-C_5$-alkyl, $C_1-C_5$-alkoxy, halogen, hydroxyl, trifluoromethyl or thienyl, or its salts with physiologically tolerated acids.

2. A therapeutic composition for the treatment of disorders associated with high blood pressure and disorders of the central nervous system, for oral administration, which comprises: from 10 to 500 mg of the 2-aminothiazole compound of claim 1, as the active ingredient, in combination with pharmaceutically acceptable auxiliaries.

3. A therapeutic composition for the treatment of disorders associated with high blood pressure and disorders of the central nervous system, for parenteral administration, which comprises: from 1 to 50 mg of the 2-aminothiazole compound of claim 1, as the active ingredient, in combination with pharmaceutically acceptable auxiliaries.

4. A method for treating high blood pressure, comprising:
administering to a subject a therapeutically effective amount of the composition of claim 2 or 3.

5. A method of treating disorders of the central nervous system, which comprises:
administering to a subject a therapeutically effective amount of the composition of claim 2 or 3.

* * * * *

UNITED STATES PATENT AND TRADEMARK OFFICE
CERTIFICATE OF CORRECTION

PATENT NO. : 5,071,864
DATED : December 10, 1991
INVENTOR(S) : Beatrice Rendenbach-Mueller, et al.

It is certified that error appears in the above-identified patent and that said Letters Patent is hereby corrected as shown below:

Title page, item [54], lines 1-3, and column 1, lines 1-3, should read,
--AMINOALKYL-SUBSTITUTED 2-AMINOTHIAZOLES AND THERAPEUTIC AGENTS CONTAINING THEM--.

Signed and Sealed this

Twentieth Day of April, 1993

*Attest:*

MICHAEL K. KIRK

*Attesting Officer*     *Acting Commissioner of Patents and Trademarks*